US00PP22349P2

(12) United States Plant Patent
Heuger

(10) Patent No.: US PP22,349 P2
(45) Date of Patent: Dec. 13, 2011

(54) ***HELLEBORUS* PLANT NAMED 'COSEH 840'**

(50) Latin Name: ***Helleborus niger*×*Helleborus argutifolius***
Varietal Denomination: COSEH 840

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 13/068,368

(22) Filed: May 9, 2011

(51) Int. Cl.
*A01H 5/00* (2006.01)

(52) U.S. Cl. ..... Plt./439

(58) Field of Classification Search ..... Plt./439
See application file for complete search history.

(56) References Cited

U.S. PATENT DOCUMENTS

| | | | | |
|---|---|---|---|---|
| PP21,063 | P2 * | 6/2010 | Heuger | Plt./439 |
| PP21,832 | P2 * | 3/2011 | Meijer | Plt./439 |
| PP22,021 | P2 * | 7/2011 | Heuger | Plt./439 |

* cited by examiner

*Primary Examiner* — Wendy C Haas
(74) *Attorney, Agent, or Firm* — C. A. Whealy

(57) ABSTRACT

A new and distinct cultivar of *Helleborus* plant named 'COSEH 840', characterized by its upright and uniformly mounded plant habit; uniform and freely flowering habit; dark green-colored leaves; long flowering period; single light yellow green and white-colored flowers;
and good garden performance.

2 Drawing Sheets

Botanical designation: *Helleborus niger*×*Helleborus argutifolius.*

Cultivar denomination: 'COSEH 840'.

BACKGROUND OF THE INVENTION

The present invention relates to a new and distinct cultivar of *Helleborus* plant, botanically known as *Helleborus niger*× *Helleborus argutifolius*, and hereinafter referred to by the name 'COSEH 840'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in November, 2003 of an unnamed proprietary seedling selection of *Helleborus niger*, not patented, as the female, or seed, parent with an unnamed proprietary seedling selection of *Helleborus argutifolius*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in February, 2006.

Asexual reproduction of the new *Helleborus* plant by divisions in a controlled greenhouse environment in Glandorf, Germany since March, 2006, has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 840'.

These characteristics in combination distinguish 'COSEH 840' as a new and distinct *Helleborus* plant:

1. Upright and uniformly mounded plant habit.
2. Uniform and freely flowering habit.
3. Dark green-colored leaves.
4. Long flowering period.
5. Single light yellow green and white-colored flowers.
6. Good garden performance.

Compared to plants of the parent selections, plants of the new *Helleborus* are more uniformly mounded and are more uniformly and freely flowering.

Plants of the new *Helleborus* can be compared to plants of *Helleborus niger*×*Helleborus lividus* 'COSEH 710', disclosed in U.S. Plant Pat. No. 21,063. In side-by-side comparisons conducted in Glandorf, Germany, plants of the new *Helleborus* differed from plants of 'COSEH 710' in growth habit as plants of the new *Helleborus* were smaller than plants of 'COSEH 710'. In addition, plants of the new *Helleborus* and 'COSEH 710' differed in flower color as plants of 'COSEH 710' had light green-colored flowers with reddish pink overtones.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 840' grown in a container.

The photograph on the second sheet is a close-up view of a typical flowering plant of 'COSEH 840'.

DETAILED BOTANICAL DESCRIPTION

The aforementioned photographs and following observations, measurements and values describe plants grown in 15-cm containers during the winter in a glass-covered greenhouse in Glandorf, Germany and under conditions which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus argutifolius* 'COSEH 840'.

Parentage:

*Female, or seed, parent.*—Unnamed proprietary seedling selection of *Helleborus niger*, not patented.

*Male, or pollen, parent.*—Unnamed proprietary seedling selection of *Helleborus argutifolius*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and uniformly mounding plant habit with flowers held just above the foliar plane; plant shape is globular; and moderately vigorous growth habit.

*Plant height.*—About 23.4 cm.

*Plant diameter* (*area of spread*).—About 33.3 cm.

Foliage Description:

*Arrangement.*—Leaves arranged in a basal rosette; leaves palmately compound with five leaflets per leaf.

*Leaf length.*—About 10.7 cm.

*Leaf width.*—About 12.6 cm.

*Leaflet length.*—About 7.3 cm.

*Leaflet width.*—About 3.9 cm.

*Leaf shape.*—Palmate; orbicular in outline.

*Leaflet shape.*—Broadly ovate to broadly elliptic.

*Leaflet apex.*—Acute.

*Leaflet base.*—Attenuate.

*Leaflet margin.*—Sharply serrate.

*Leaflet texture, upper and lower surfaces.*—Smooth, glabrous; leathery.

*Leaflet venation pattern.*—Pinnate.

*Leaflet color.*—Developing leaves, upper surface: Close to 137B. Developing leaves, lower surface: Close to 138A. Fully developed leaves, upper surface: Between 147A and 189A; venation, close to 144A. Fully developed leaves, lower surface: Close to 147B; venation, close to 145A to 145B.

*Petiole.*—Length: About 7.5 cm. Diameter: About 5 mm. Texture, upper and lower surfaces: Smooth, glabrous. Color, upper and lower surfaces: Close to 144C.

Flower description:

*Flower shape and habit.*—Single rotate flowers arranged in terminal and axillary cymes; freely and uniform flowering habit with about 56 flowers and flower buds per plant; flowers facing outwardly to slightly nodding and slightly upright.

*Fragrance.*—None detected.

*Natural flowering season.*—Plants begin flowering about ten months after planting; long flowering period; plants flower from late winter to early spring in Germany.

*Flower longevity on the plant.*—About ten days; flowers not persistent.

*Flower buds.*—Length: About 1.9 cm. Diameter: About 1.3 cm. Shape: Ovate. Color: Close to 145C to 145D.

*Inflorescence height.*—About 23.8 cm.

*Inflorescence diameter.*—About 15.3 cm.

*Flower diameter.*—About 6.9 cm.

*Flower depth* (*height*).—About 2.4 cm.

*Petals.*—Transformed into nectaries.

*Sepals.*—Quantity and arrangement: Five arranged in a single whorl. Length: About 3.4 cm. Width: About 2.5 cm. Shape: Broadly ovate to broadly elliptic. Apex: Rounded. Margin: Entire. Texture, upper and lower surfaces: Smooth, glabrous. Color: When opening, upper surface: Close to 145C to 145D; towards the base, close to 145B. When opening, lower surface: Close to 145C; towards the margins, close to 145D; towards the base, close to 145A. Fully opened, upper surface: Close to 145D; towards the margins, close to 157D; towards the base, close to 145B; with development, color becoming closer to 145A. Fully opened, lower surface: Close to 145C to 145D; towards the base, close to 145A.

*Peduncles.*—Strength: Moderately strong. Length: About 17.2 cm. Diameter: About 6 mm. Aspect: About 10° from vertical. Texture: Smooth, glabrous. Color: Close to 144C moderately dotted with close to 152B to 152D.

*Pedicels.*—Strength: Moderately strong. Length: About 6 cm. Diameter: About 2 mm. Aspect: Erect to about 30° from the peduncle axis. Texture: Smooth, glabrous. Color: Close to 145C.

*Reproductive organs.*—Stamens: Quantity per flower: About 100. Filament length: About 1.6 cm. Filament color: Close to 157D. Anther shape: Reniform. Anther length: About 1.5 mm. Anther color: Close to 150C. Pollen amount: Scarce. Pollen color: Close to 158D. Pistils: Quantity per flower: About five. Pistil length: About 1 cm. Stigma shape: Club-shaped. Stigma color: Close to 145C. Style length: About 9 mm. Style color: Close to 157C to 157D. Ovary color: Close to 145C. Nectaries (transformed petals): Quantity per flower: About 15. Length: About 1 cm. Diameter, apex: About 2 mm. Diameter, base: About 1 mm. Shape: Flattened triangular. Color: Close to 144A to 144B; towards the apex, close to N144B.

*Seeds/fruits.*—Seed and fruit development have not been observed.

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen/pest resistance: Plants of the new *Helleborus* have not been shown to be resistant to pathogens and pests common to *Helleborus*.

It is claimed:

1. A new and distinct *Helleborus* plant named 'COSEH 840' as illustrated and described.

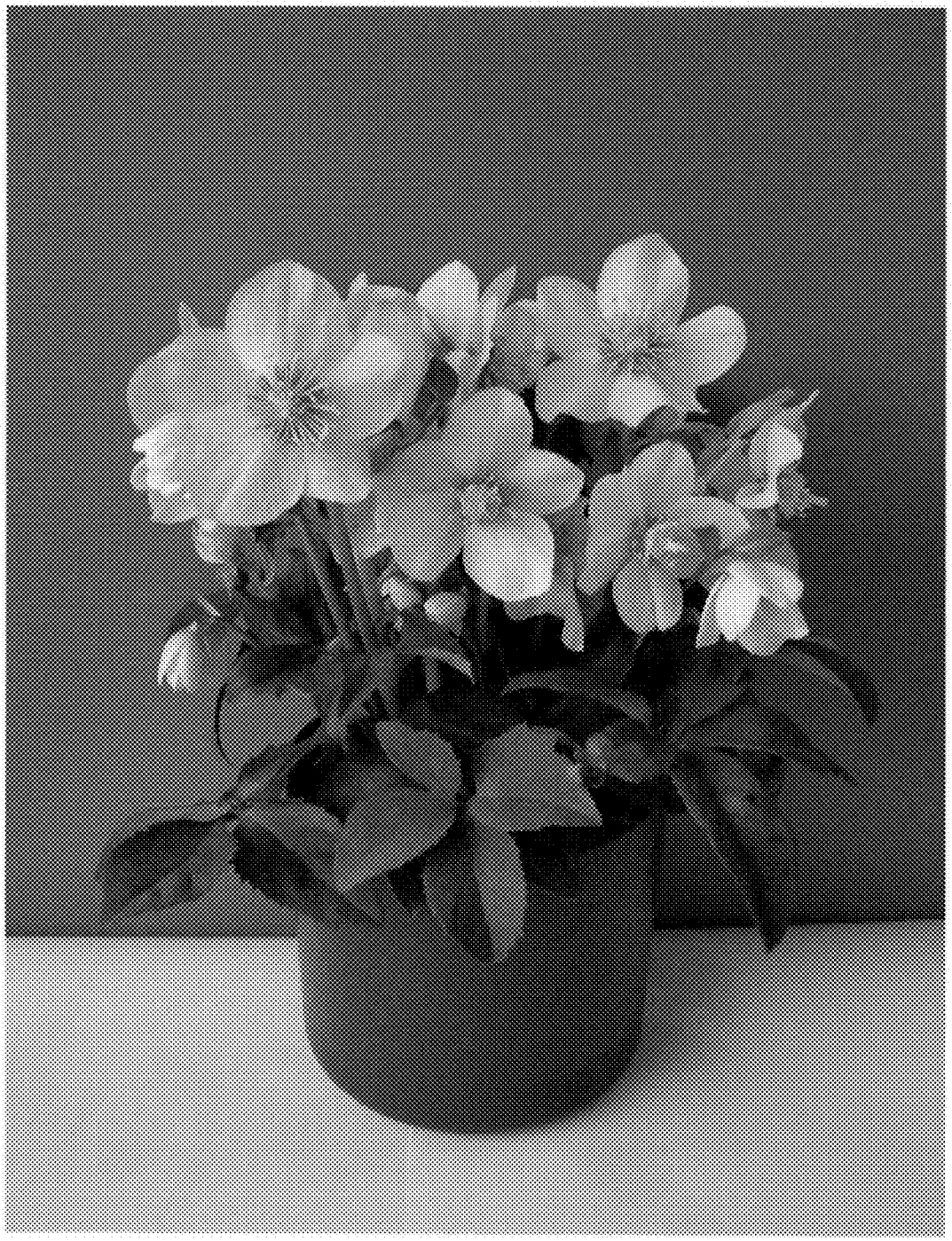

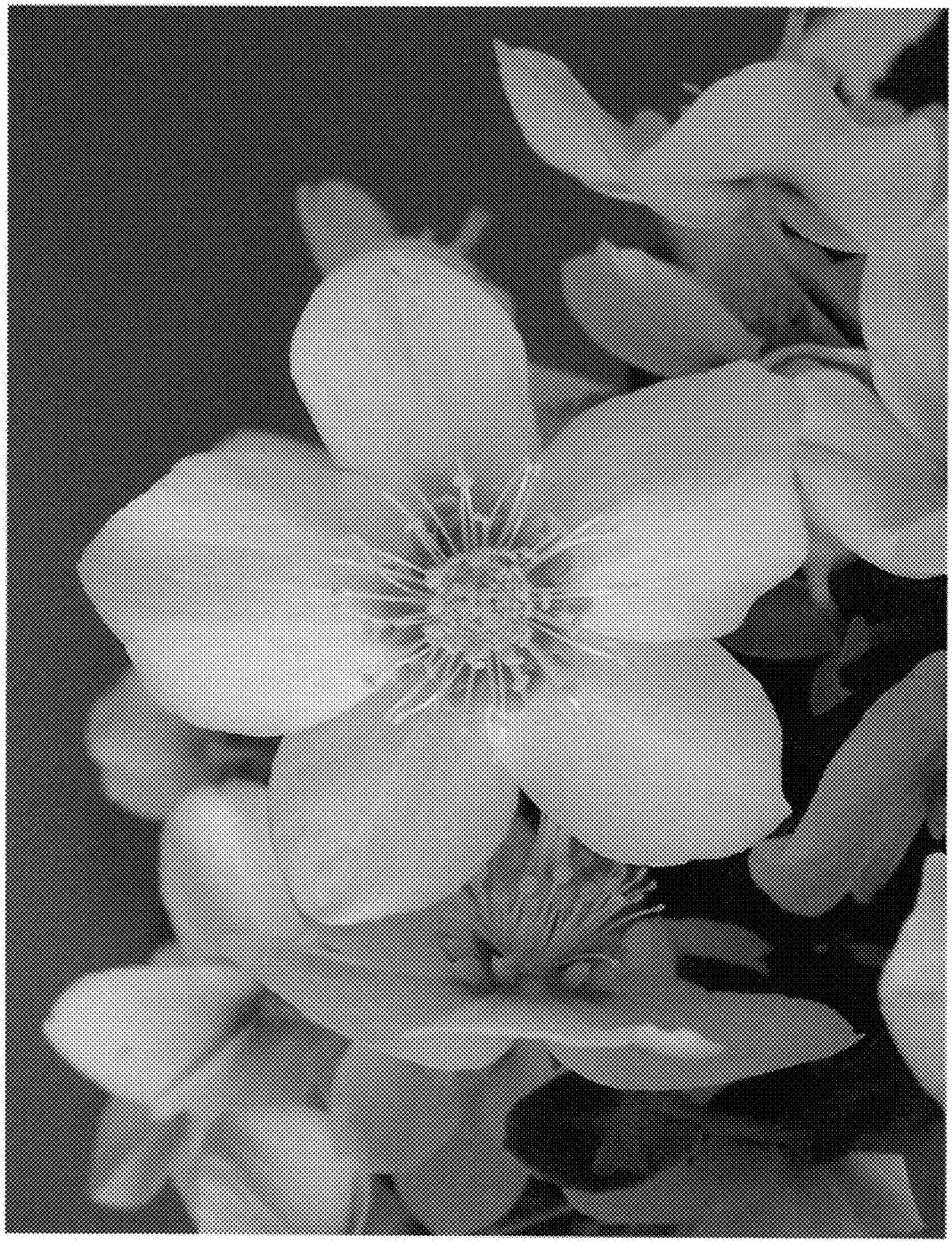

* * * * *